United States Patent [19]

Jackson

[11] Patent Number: 4,916,210

[45] Date of Patent: Apr. 10, 1990

[54] RESIN FROM ALPHA, ALPHA', ALPHA"-TRIS(4-CYANATOPHENYL)-1,3,5-TRIISOPROPYLBENZENE

[75] Inventor: Roy J. Jackson, Houston, Tex.

[73] Assignee: Shell Oil Company, Houston, Tex.

[21] Appl. No.: 260,346

[22] Filed: Oct. 20, 1988

[51] Int. Cl.$^4$ .............................................. C08G 83/00
[52] U.S. Cl. .................................. 528/422; 427/385.5; 428/411.1; 428/473.5; 524/612; 525/422; 525/426; 528/322
[58] Field of Search ............... 528/422, 322; 525/422, 525/426

[56] References Cited

U.S. PATENT DOCUMENTS

| | | | |
|---|---|---|---|
| 3,595,900 | 7/1971 | Loudas et al. | 260/453 |
| 3,738,962 | 6/1973 | Loudas et al. | 260/47 |
| 3,755,402 | 8/1973 | Grigat et al. | 260/453 |
| 3,954,693 | 5/1976 | Fong | 260/37 |
| 4,110,364 | 8/1978 | Gaku et al. | 528/170 |
| 4,157,360 | 6/1979 | Prevorsek | 260/860 |
| 4,403,073 | 9/1983 | Ikeguchi | 525/374 |
| 4,554,346 | 11/1985 | Gaku et al. | 528/363 |
| 4,709,008 | 11/1987 | Shimp | 528/422 |
| 4,749,760 | 6/1988 | Wang | 525/471 |

*Primary Examiner*—Harold D. Anderson

[57] ABSTRACT

Alpha, alpha', alpha"-tris(4-cyanatophenyl)-1,3,5-triisopropylbenzenes are new and useful for preparing high heat resistant resins having a low dielectric constant, particularly for electrical applications.

15 Claims, No Drawings

RESIN FROM ALPHA, ALPHA', ALPHA"-TRIS(4-CYANATOPHENYL)-1,3,5-TRIISOPROPYLBENZENE

FIELD OF THE INVENTION

The present invention relates to novel alpha, alpha', alpha"-tris(4-cyanatophenyl)-1,3,5-triisopropylbenzenes and resins thereof.

BACKGROUND OF THE INVENTION

Cyanato resins are occasionally found in the art for use in adhesives, coatings and the like. U.S. Pat. No. 3,595,900 and a division thereof 3,738,962 describe cyanatophenyl-terminated polyarylene ethers. U.S. Pat. Nos. 3,755,402; 4,110,364; 4,157,360; 4,403,073; and 4,554,346 describe other cyanato esters and resins thereof—including mixtures thereof with (1) a bismaleimide, (2) a thermoplastic polymer, (3) certain polybutadiene, and optionally a maleimide or (4) a hydroxy unsaturated compound. These resins generally describe relatively linear components having only one or two aromatic rings which may or may not be separated by ether oxygens.

There is a need in electrical applications for unique resins having a low dielectric constant, high solubility and low moisture uptake as well as a high glass transition temmperature (Tg) in cured laminates, particularly in those applications where a fast electrical signal time is required as in advanced computer circuitry and the present invention is directed to new resins possessing such a desirable combination of properties.

SUMMARY OF THE INVENTION

The present invention is directed to novel alpha, alpha', alpha"-tris(4-cyanatophenyl)-1,3,5-triisopropylbenzenes of Formula I:

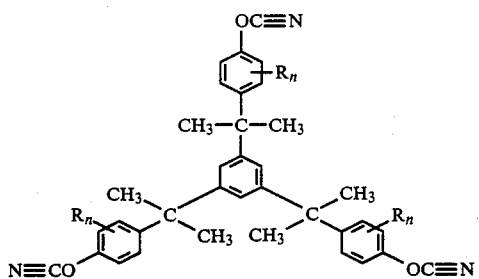

wherein in each R is independently an alkyl group containing from 1 to 4 carbon atoms, preferably a methyl group, and each n is independently 0, 1 or 2.

The compounds of Formula I are prepared by treating the corresponding known alpha, alpha', alpha"-tris (4-hydroxyphenyl)-1,3,5-triisopropylbenzenes (Kennedy and Kline Co.) with a compound which will react with a hydroxy group to yield a cyanate group, e.g., a cyanogen halide such as cyanogen bromide or the like. A slight excess of cyano reactant is preferred.

The reaction is conducted in the presence of a base including alkali metal hydroxides, aliphatic amines and the like, such as triethylamine, sodium hydroxide or the like. It is preferred to adjust the addition rate of the base during the reaaction such that always an excess of cyanogen halide over base is present. so that there is always an excess of cyanogen halide over the base.

The reaction is conducted at low temperatures in view of the exothermic nature of the reaction and the volatility of the cyanogen halide. For example, the temperature is from about −40° C. to about 40° C., preferably about −20° C. to about 10° C. The use of conventional inert liquid organic solvents is preferred, including aromatic hydrocarbons, such as benzenes, toluene or xylene; ethers, such as hydrocarbons, such as methylene chloride or chlorobenzene; alcohols, such as methanol, ethanol, or isopropyl alcohol; ketones, such as acetone, methyl ethyl ketone, methyl isobutyl ketone and the like.

The invention also includes a curable resin composition comprising (a) at least one cyanate aromatic ester according to Formula I or a prepolymer of the cyanate ester optionally with an amine, and optionally one or more of (b) a copolymer of (1) with at least one or more of
  (1) a second cyanate ester, or a prepolymer thereof optionally with an amine;
  (2) an amine; and/or (c) a maleimide component, a prepolymer of a maleimide or a coprepolymer of a maleimide and an amine.

Because of their unique combination of properties, such curable resin compositions are useful in the preparation of various articles of manufacture. Thus, the invention also includes prepregs of the above composition as well as shaped articles, reinforced compositions, electrical laminates and the like as hereinafter described from cured or partially cured above resin compositions of the compound of Formula I of the invention.

Thus, the cyanate compound of Formula I of the present invention in which n is zero is particularly useful as a monomer, intermediate or prepolymer for the preparation of cyanate polymers. Polymerization of the cyanates is accomplished by heating the cyanates of Formula I to effect their thermal polymerization. Homopolymers of the cyanates of Formula I as well as copolymers of two or more cyanates can be prepared in this fashion.

The thermal polymerization of the cyanates, in accordance with this invention, involves trimerization of terminal cyanato groups to form a cyanate that has a three-dimensional network structure with polyarylene linkages between cyanate rings, the polymerization being illustrated in Formula II:

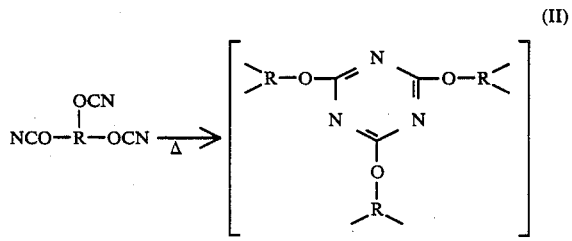

where R is the tris(4-hydroxyphenyl)-1,3,5-triisopropylbenzene residue of the cyanate defined in Formula I above.

Generally, the polymerization or curing of cyanates, in accordance with this invention, will be carried out by first melting the cyanate monomeric material to obtain a homogeneous melt or dissolving in a suitable solvent such as an alcohol, ketone, ester, aromatic hydrocarbon or the like and then raising the temperature to a range of about 0° to 300° C., preferably 100° to 250° C. Alternatively, this polymerization can be carried out at lower temperatures with the aid of known cyanate polymerization activators, initiators or catalysts. These polymerization promoting agents representatively include Lewis acids, such as aluminum chloride, boron trifluoride, ferric chloride, titanium chloride, and zinc chloride; protonic acids, such as hydrochloric and other mineral acids; salts of weak acids, such as sodium acetate, sodium cyanide, sodium cyanate, potassium thiocyanate, sodium bicarbonate, sodium boronate, and phenylmercuric acetate; and bases, such as sodium methoxide, sodium hydroxide, pyridine, triethylamine, and the like. Preferred catalysts are non-ionic coordination compounds, such as cobalt, iron, zinc, and copper acetyl acetonates. The amount of catalyst used can vary, and generally will be about 0.05 to 5 mole percent, preferably about 0.05 to 0.5 mole percent.

The polymerization of the cyanates can also be carried out by polymerizing them in solution or in suspension, using as a solvent or suspension medium the common organic solvents such as hydrocarbons, ketones, halogenated hydrocarbons, nitrated hydrocarbons, dimethylsulfoxide, dimethylformamide, ether or the like. The solvent can be removed by distillation or simple evaporation during the course of or at the end of the polymerization.

The various triscyanates of Formula I and (co)polymers thereof of the invention are crystalline or amorphous solids which melt to flowable liquids at convenient working temperatures. They are soluble in a variety of organic solvents such as methylene chloride, chloroform, benzene, toluene, chlorobenzene, acetone, methyl ethyl ketone, ethyl benzoate, ethyl cellulose, dimethylformmide, and the like. They provide excellent bases for solvent-diluted coatings such as brush, spray, and dip coatings, particularly in the case of the higher molecular weight prepolymers. They can be used as one-component cured-in-place resins which show good thermal stability along with resistance to solvents and corrosive chemicals such as dilute acids, and basis. The fabrications of shaped articles from these cyanate (co)-polymers is greatly facilitated in that no volatile by-products are liberated during the curing process.

The (co)polymers of this invention have relatively high molecular weight and consequently have low volatility and therefore less toxicity and can be conveniently handled at elevated temperatures. Also, reactions involving these cyanates can be controlled readily, in spite of exothermic heat generated, since the active cyanato groups constitute in part a small portion of the overall compound. The cyanate (co)polymers of this invention have improved strength, toughness, and impact resistance and can be used for adhesives, coatings and binders. Resistance to thermal degradation caused by aging at high temperatures is also improved because of a reduced concentration of the relatively less stable cyanate rings.

It is also within the scope of this invention to copolymerize the triscyanate of Formula I with one or more mono or dicyanate esters of the type already well known in the prior art. Preferred are aromatic cyanate esters and such comonomers useful in this invention for this purpose include those of formula III:

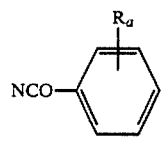

(III)

where a is 0 or 1 and R is a cyanato or an aromatic group such as benzene, naphthalene, or biphenyl, which group can have a cyanato group as a ring substituent. The amount of such aromatic cyanate of Formula III which can be copolymerized with the triscyanates of this invention can vary and generally will be dictated by the particular properties desired to be imparted by them to the cyanate copolymers. For example, the degree of crosslinking of the copolymer can be increased in some instances by incorporating such aromatic short chain (di)cyanates. The heat distortion temperature of the copolymer can thereby be increased.

Where a monocyanate is copolymerized with the triscyanate of the invention, copolymeric cyanates are formed in which the network growth and crosslinking density are reduced by the chain-terminating monocyanate monomer. Generally, where used, the second cyanate [component (b1)] will amount to 5 to 95 wt. percent, preferably 5 to 50 wt. percent of the cyanate copolymer.

The triscyanates of the invention can also be used in the form of a prepolymer. The prepolymer is prepared by polymerizing the polyfunctional cyanate monomer in the presence of a conventional catalyst, for example, a mineral acid, a Lewis acid, a salt such a sodium carbonate or lithium chloride, or a phosphoric acid ester such as tributyl phosphine. The prepolymer contains a triazine ring generally in the molecular as a result of the trimerization of the cyano group of the tricyanate. Preferred prepolymers are those having an average molecular weight of at least 400, especially up to 600.

The cyanate ester comonomer can be used in the form of a mixture of the monomer and the prepolymer. For example, many of the commercially available cyanate esters derived from bisphenol A and cyanogen halide are in the form of mixtures of cyanate monomers and prepolymers, and such materials can also be used in the present invention.

A mixture of a prepolymer of the cyanate ester comonomer and an amine may also be used.

Generally, the cyanate ester comonomers can be prepared by known methods including reacting polyhydric phenolic materials with cyanogen halides, such as cyanogen chloride or cyanogen bromide. Cyanate aromatic esters, which are readily available and preferred for use as comonomers in this invention in view of the properties of the final resin obtained, are those prepared by reacting a symmetrical, fused ring-free dihydric phenol, such as bisphenol A (2,2-bis[4'-hydroxyphenyl]propane) with cyanogen halides. Likewise, cyanate aromatic esters obtained by the reaction of a phenolformaldehyde precondensate with cyanogen halides can be advantageously used. Suitable cyanates disclosed in U.S. Pat. Nos. 4,110,364; 3,595,900; 3,755,402; 4,157,360; 4,403,073; German Pat. Nos. 1,190,184 and 1,195,764; and *Angew Chemie* 76, 303 (1964); and *Acta Chem. Scand.* 18, 826 (1964), the disclosures of which are incorporated by reference.

The optional maleimide component of the curable resin composition of this invention, hereinafter referred to as component (c) is selected from maleimides, prepolymers thereof and prepolymers of the maleimides and amines.

The maleimides employed in the present invention are conventional organic compounds known in the art having two maleimide groups derived from maleic anhydride and diamines or polyamines. Suitable maleimides include bismaleimides represented by the following formula (1)

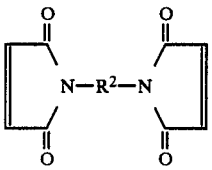

wherein $R^2$ represents a divalent aromatic (aryl), aliphatic or alicyclic organic group containing about 2 to 40 carbon atoms.

Examples of the divalent organic group $R^2$ in the formula (1) include: (i) aromatic, aliphatic or alicyclic hydrocarbon groups containing 3 to 20 and, preferably, 6 to 16 carbon atoms such as isopropylidene, phenylene, naphthylene, xylene, cyclohexylene or hexahydroxylylene; and (ii) organic groups consisting of a plurality of aromatic rings bonded to each other directly or through a bridging atom or group, for example, those expressed by the following formula (2)

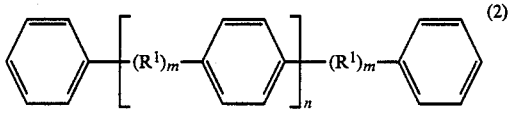

wherein each m is independently zero or 1, n is zero or 1; and each $R^1$ is independently a divalent aliphatic or aromatic hydrocarbon group containing up to 14 carbon atoms, an oxygen atom, a sulfur atom, a carbonyl group, a sulfonyl group, a sulfinyl group, an alkyleneoxyalkylene group containing up to 4 carbon atoms in each alkylene group, an imino group,

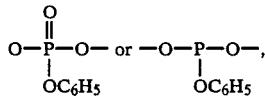

or (iii) groups derived from novolac-type phenol or resorcinol resins. In formula (1), the divalent organic group $R^2$ may contain an organic group which does not participate in the reaction, such as an alkyl group containing 1 to 4 carbon atoms (e.g., methyl or ethyl), or an alkoxy group containing 1 to 4 carbon atoms (e.g., methoxy or ethoxy), at the aromatic ring when it is an aromatic organic group or at the alicyclic ring when it is an alicyclic organic group. Suitable polymaleimides are derived from maleimides and polyamines. Preferably, the maleimide is methylene dianiline bismaleimide.

Examples of suitable organic groups of formula (2) are those derived from biphenyl, diphenylmethane, alpha,alpha-dimethylphenylmethane, diphenyl ether, diphenyl dimethylene ether, diphenyl thioether, diphenyl ketone, diphenyl thioether, diphenylamine, diphenyl sulfoxide, diphenyl sulfone, triphenyl phosphite, and triphenyl phosphate and the like.

The maleimide can be prepared by a method known per se which comprises reacting maleic anhydride with diamines or polyamines, and then cyclodehydrating the resulting maleamidic acids. The amines are preferably aromatic diamines in view of the thermal stability of the final resins. When it is desired to improve the flexibility or suppleness of the resin, alicyclic diamines may be used alone or in combination with the aromatic diamines. From the viewpoint of reactivity, the diamines are preferably primary diamines, but secondary diamines can also be used. Examples of suitable diamines are m-phenylene diamine, m-, or p-xylylenediamine, 1,4-cylohexanediamine, hexahydroxylylene diamine, 4,4'-bisaminophenyl methane, 4,4'-bisaminophenyl sulfone, bis(4-amino-3-methylphenyl) methane (MDT), bis(4-amino-3,5-dimethylphenyl)methane (MDX), 4,4'-bisaminophenylcyclohexane, 4,4'-bisaminophenyl ether, 2,2'-bis(4'-aminophenyl)propane, 2,2'-bis(4-amino-3-methylphenyl)methane, α,α-bis(4-aminophenyl)phenylmethane, α,α'-bis(4-aminophenyl)-p-diisopropylbenzene and the like.

The maleimides can be used either alone or in admixture of two or more.

Prepolymers of the maleimides, and, preferably, prepolymers of the maleimides and amines can also be used.

As already stated, an amine can be incorporated in the form of a prepolymer of the polyfunctional cyanate ester and the amine as component (b) or a prepolymer of the maleimide component and the amine component (c). Examples of the amines that can be used in this invention include (i) diamines of the general formula (3)

$$H_2N-R^3-NH_2 \qquad (3)$$

wherein $R^3$ is a divalent aromatic or alicyclic organic group, especially those illustrated with regards to the production of maleimides, and (ii) polyamines such as hexamethylene tetramine, polyethylene imine, polyamino styrene or polyvinyl imidazole; triethylene diamine; imidazoles such as 2-methylimidazole, 2-undecylimidazole, 2-heptadecylimidazole, 2-phenylimidazole, 2-ethyl-4-methylimidazole, 1-benzyl-2-methylimidazole, 1-propyl-2-methylimidazole, 1-cyanoethyl-2-methylimidazole, 1-cyanoethyl-2-ethyl-4-methylimidazole, 1-cyanoethyl-2-undecylimidazole, 1-cyanoethyl-2-phenylimidazole or 1-guanaminoethyl-2-methylimidazole, adducts formed between these imidazoles and trimellitic acid and like polyamines.

When the above-mentioned amines are used in the form of a prepolymer with maleimides, the prepolymer can be produced by reacting the maleimide and the amine, especially 1 mol of the maleimide and ½ to 1 mol of the diamine, in a suitable solvent such as ketones under the known conditions, for example, by heating at a temperature of about 40° to 250° C. for 5 minutes to 5 hours. The prepolymer derived from the maleimide and the amine, although differing according to the ratio of the monomers or the degree of poly addition, are considered to have the structure represented by the following formula (4)

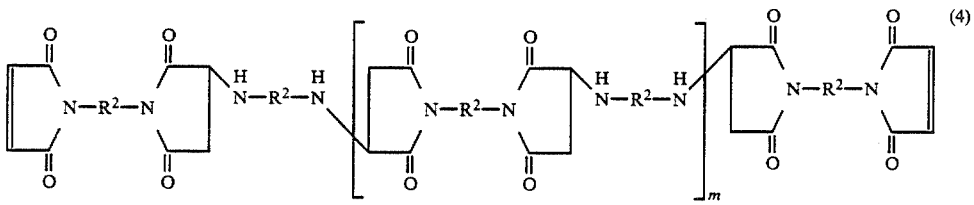

wherein m is zero or a positive number, generally not more than 10, and $R^2$ is the same as defined hereabove.

When the amines are incorporated in the composition in the form of prepolymers with the cyanate ester, the prepolymers can be produced by reacting the cyanate ester monomer with the diamines, preferably using 0.1 to 1 equivalent of the diamines based on the cyanate ester monomer, in a suitable solvent such as ketones at a temperature of about 0° to 100° C. for 1 minute to 1 hour.

In either of these cases of adding amines in the form of prepolymers, it is of course permissible to cause free amines to be present in the composition.

When the amines are included in component (b) and/or component (c) in the form of a prepolymer or the like, they are considered to function mainly as a modifier for polymer such as a chain extender.

Suitable maleimides for component (c) are disclosed in U.S. Pat. Nos. 4,110,364, 4,298,720, and the like, which are incorporated herein by reference.

The components of the curable resin (co)polymer composition of this invention can be varied over a wide range. Generally, however, the ratio by weight of cyanate component (a) and optionally (b) and/or maleimide component (c) is in the range of from about 1:99 to about 99:1, preferably about 5:95 to about 95:5. When preparing heat resistant resin having good toughness, from about 10% by weight of cyanate component to about 90% by weight of cyanate component, preferably about 10% to about 50% by weight, is used on the basis of total weight of all polymerizable components. In order to improve heat resistance of cured resin derived from the cyanate component, it is preferably to use a combined weight of maleimide components ranging from about 10–90% by weight, preferably about 10% to about 50% by weight, based on the total weight of all polymerizable components.

The curable composition of this invention comprises one or more components which can each be used in any desired form such as solid, solution or dispersion. These components are mixed in solvent or in the absence of a solvent to form the compositions of this invention. For example, the mixing procedure comprises mixing solutions of cyanate component and maleimide or either separately or together in a suitable inert organic solvent, such as for example, ketones such as methyl ethyl ketone, chlorinated hydrocarbons such as methylene chloride, ethers and the like, and homogenizing the resulting mixed solution at room temperature or at an elevated temperature below the boiling point of the solvents to form a composition in the form of a solution. When homogenizing these solutions at room temperature or at an elevated temperature, some reactions may take place between the constituent elements. So long as the resins components are maintained in the state of solution without gelation, such reactions do not particularly affect the operability of the resulting composition in, for example, a bonding, coating, laminating or molding operation.

The curable resin compositions of invention can be used in the above solution form as adhesives, paint vehicles, molding materials to be impregnated in substrates, or laminating materials. In this case, the concentration of the resin solid in the solution is determined so that the optimum operability can be obtained according to the desired utility.

The resin compositions of this invention can be used for various purposes in the form of dried powder, pellets, resin-impregnated product or compound. For example, compositions with the individual components uniformly mixed can be obtained by uniformly mixing the resin components in solution, and then removing the solvents from the homogeneous solution at reduced pressure or at an elevated temperature. Alternatively, solids components are kneaded at room temperature or at an elevated temperature to form a homogenized resin composition.

The curable composition of this invention may be reticulated by heating it alone to form a cured resin having heat resistance. In general, a catalyst may be used in order to promote crosslinking reaction of the components in the composition.

Examples of the catalysts include imidazoles, such as 2-methylimidazole, 2-undecylimidazole, 2-heptadecylimidazole, 2-phenylimidazole, 2-ethyl-4-methylimidazole, 1-benzyl-2-methylimidazole, 1-propyl-2-methylimidazole, 1-cyanoethyl-2-methylimidazole, 1-cyanoethyl-2-ethyl-4-methylimidazole, 1-cyanoethyl-2-undecylimidazole, 1-cyanoethyl-2-phenylimidazole, 1-guanaminoethyl-2-methylimidazole and addition product of an imidazole and trimellitic acid; tertiary amines, such as N,N-dimethyl benzylamine, N,N-dimethylaniline, N,N-dimethyltoluidine, N,N-dimethyl-p-anisidine, p-halogeno-N,N-dimethyl-aniline, 2-N-ethylanilino ethanol, tri-n-butylamine, pyridine, quinoline, N-methylmorpholine, triethanolamine, triethylenediamine, N,N,N',N'-tetramethylbutanediamine, N-methylpiperidine; phenols, such as phenol, cresol, xylenol, resorcinol, and phloroglucin; organic metal salts, such as lead naphthenate, lead stearate, zinc naphthenate, zinc octoate, tin oleate, dibutyl tin maleate, manganese naphthenate, cobalt naphthenate, and acetylacetone iron; and inorganic metal salts, such as stannic chloride, zinc chloride and aluminum chloride; peroxides, such as benzoyl peroxide, lauroyl peroxide, octanoyl peroxide, acetyl peroxide, para-chlorobenzoyl peroxide and di-t-butyl diperphthalate; acid anhydrides, such as maleic anhydride, phthalic anhydride, fumaric anhydride, pyromellitic anhydride, trimellitic anhydride, hexahydrophthalic anhydride, hexahydropyromellitic anhydride and hexahydrotrimellitic anhydride; azo compounds, such as azoisobutylonitrile, 2,2'-azobispropane, m,m'-azoxystyrene, hydrozones, and mixtures thereof. The amount of catalyst varies considerably according to the type of catalyst, the utility or during conditions. They can, however, be used in catalytic amounts such as, for example, less than 5% by weight of the total composition. The use of zinc octoate is preferred.

A variety of additives may be added to the curable composition to impart specific properties provided that they do not impair the essential properties of the resulting resin. Examples of the additives include natural or synthetic resins, fibrous reinforcement, fillers, pigments, dyestuffs, thickening agents, wetting agents, lubricants, flame-retardants and the like.

The resin composition of this invention can also contain a white pigment such a titanium dioxide, a colored pigment such as yellow lead, carbon black, iron black, molybdenum red, prussian blue, ultramarine, cadmium yellow or cadmium red, and other various organic or inorganic dyes and pigments in order to color the compositions. In addition to the above colored pigments, the resin compositions can also contain a rust-proofing pigment such as zinc chromate, red lead, red iron oxide, zinc flower or strontium chromate, an anti-sag agent such as aluminum stearate, a dispersing agent, a thickener, a coat modifier, a body pigment or a fire retardant, which are known additives for paints.

The monomers will usually contain an amount of a polymerization inhibitor effective to prevent premature polymerization of the monomer, generally less than about 0.5 weight percent, usually less than about 0.2 weight percent, based on the weight of the monomer. Examples of suitable inhibitors include tertiary butyl catechol, benzoquinone, hydroquinone and phenothiazine.

The composition is suitable for fiber-reinforced composites applications, for which a fibrous reinforcing material, such as chopped glass, glass fibers, carbon fiber, and the like, in the form of a mat, cloth or continuous fibers, for example, is impregnated with the resin system. The impregnated fibers are usually subjected to a relatively mild heat treatment ("B-staged") to partially cure the resin to a flexible, tacky state, or "prepreg." The prepreg is then subjected to elevated temperature and pressure so as to completely cure the resin to hard, inflexible state. A plurality of prepregs can be layered and cured to form a laminate having utility in circuit boards. For such electrical applications, the properties of flame retardants and high Tg are important.

The compositions of this invention are cured by heating after applying it to a substrate as a coating or adhesive layer, or after molding or laminating in the form of powder, pellet or as impregnated in a substrate. The curing conditions of the curable composition of this invention depend on the proportion of components constituting the composition and the nature of the components employed. In general, the composition of this invention may be cured by heating it at a temperature within the range of about 0°–300° C., preferably about 100° C.–250° C., although differing according to the presence of a catalyst or curing agent or its amount, or the types of the components in the composition. The time required for heating is generally 30 seconds to 10 hours, although considerably differing according to whether the resin composition is used as a thin coating or as molded articles of relatively large thickness or as laminates or as matrix resins for fiber reinforced composites, particularly for electrical and electronic applications, e.g., when applied to an electrically nonconductive material and subsequently curing the composition. Suitable fibrous reinforcing materials include glass fibers, quartz fibers, carbon fibers, boron fibers, Kevlar fibers, Teflon ® fibers and the like, with woven or continuous glass fibers or carbon fibers being preferred. The fibrous or reinforcing material is present in the composition in an amount effective to impart increased strength to the composition for the intended purpose, generally from about 40 to about 95 weight percent, usually from about 50 to about 80 weight percent, based on the weight of the total composition. The laminates of the invention can optionally include one or more layers of a different material and in electrical laminates this can include one or more layers of a conductive material such as copper or the like. When the resin composition of this invention is used for producing molded articles, laminated articles or bonded structures, the curing is desirably effected under pressure. Generally, this pressure is from 10 to 100 $Kg/cm^2$ (gauge).

The composition of this invention cures rapidly, even under mild conditions, so is especially suitable when quantity production and ease of workability are desired. The cured resin made from the composition not only has excellent adhesive force, bond strength, heat resistance, and electric properties, but also is excellent in mechanical properties and resistance to impact, chemicals, moisture and the like. The composition of this invention has a variety of uses as a coating material for rust prevention, flame resistance, flame retardants and the like; as electrical insulating varnish; as adhesive; in laminates to be used for furnitures, building materials, sheathing materials, electrical materials especially where low dielectric content and good thermal properties are desired in a variety of moldings and the like.

ILLUSTRATIVE EMBODIMENTS

The present invention is further illustrated by the following examples which are not intended to be construed as limitations upon the invention.

EMBODIMENT 1

Tricyanate Ester

Alpha, alpha', alpha"-tris(4-hydroxylphenyl)-1,3,5-triisopropylbenzene (1) was obtained from Mitsui Petrochemical Company and used without further purification. Into a five-liter, four-neck round-bottom flask equipped with a stirring rod, thermocouple, condenser, and an addition funnel was added 381.6 grams of cyanogen bromide in 1500 ml of isopropyl alcohol. The solution was cooled to 5° C. In a separate container 480 grams of (1) was dissolved in 1000 ml of isopropyl alcohol and cooled to 5° C. To the latter 233.9 grams of triethylamine was added with stirring. When the triethylamine addition had been completed, the entire mixture was transferred to the dropping funnel and added dropwise to the cyanogen bromide-isopropyl alcohol solution. Care was exercised to maintain the temperature at 5° C. or below. After the addition had been completed, the reaction was left to stir overnight and gradually come to room temperature. The triscyanate ester which had crystallized out with the triethylamine hydrobromide salt was washed several times with water and dried in a vacuum oven at 50° C. to remove the water. The yield was 300 grams. The product was confirmed by both IR and NMR.

EMBODIMENT 2

Laminate

A varnish solution was prepared by dissolving 72 grams of the triscyanate ester in 36 mls of acetone and 2 mls of dimethyl formamide. 0.2 PHR (parts per hundred parts by weight based on the ester) of zinc octoate (8% solution) was added as a catalyst. The varnish had a gel time of 85 seconds on a hot plate at 171° C. The varnish solution was coated on 7628 glass cloth and advanced to a ("B") stage in a forced air oven set at 163° C. for three minutes. The prepreg dust had a gel time of 28 seconds at 171° C. Eight layers of the prepregs were stacked and pressed into a laminate at 180° C. and 25 PSI pressure for 1 hour. The cured laminate was postcured for 2 hours at 220° C. The electrical and thermal properties of the laminate (Table 1) were found to be outstanding.

TABLE 1

Electrical and Thermal Properties of a Laminate of Triscyanate Ester Resin

| | |
|---|---|
| Flexural Strength, 23° C., psi | 54592 |
| Flexural Modulus, 23° C., psi | 2530300 |
| Dielectric Constant, 23° C., D-24/23 | 3.8 |
| Dissipation Factor, 23° C., D-24/23 | 0.0083 |
| Dielectric Strength, 23° C., V/mil | 705 |
| Volume Resistivity ($\times 10^{15}$ ohm-cm) | 1.46 |
| Surface Resistivity ($\times 10^{15}$ ohm-cm) | 6.86 |
| Water Absorption, % wt, 1 hr 15 psi Steam | 0.24 |
| Tg, DMA* Max Damping, °C. | 265 |
| Tg, DSC,** °C. | 214 |

*Dynamic mechanical analyzer.
**Differential scanning calorimeter.

The properties of the above laminate prepared from the new triscyanate ester are quite useful, particularly the thermal properties and the dielectric constant.

What is claimed is:

1. A curable resin composition comprises:
   (a) at least one cyanate aromatic ester of the formula I

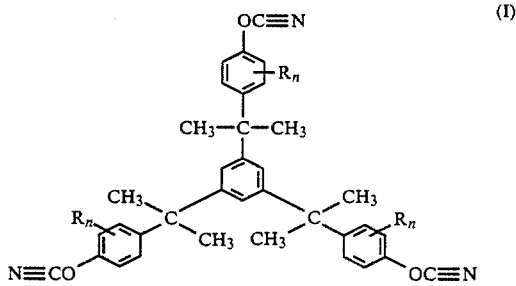

wherein in each R is independently an alkyl group containing from 1 to 4 carbon atoms, and each n is independently 0, 1 or 2, a prepolymer of the cyanate ester (I), a prepolymer of the cyanate ester (I) with an amine; (a) alone or with one or more of
   (b) a copolymer of the ester of formula I with at least one or more of
      (1) a second mono- or polycyanate aromatic ester, a prepolymer of said second cyanate aromatic ester, or a prepolymer of said second cyanate aromatic ester with an amine;
      (2) an amine; and
   (c) a maleimide component, a prepolymer of a maleimide or a coprepolymer of a maleimide and an amine.

2. A curable resin according to claim 1 wherein (a) is a cyanate ester prepolymer.

3. A curable resin according to claim 1 wherein a second cyanate ester (b) is present as an aromatic cyanate.

4. A curable resin according to claim 1 wherein the maleimide component is a monomer.

5. A curable resin according to claim 4 wherein the monomer is methylene dianiline bismaleimide.

6. A curable resin according to claim 1 wherein the maleimide is a prepolymer of a maleimide and a diamine.

7. A curable resin according to claim 1 wherein (a) is a cyanate ester, a prepolymer of said cyanate ester, or a prepolymer of said ester in admixture with the monomer; (a) alone or with one or more of (b) a second aromatic cyanate ester, and (c) a maleimide or a prepolymer of a maleimide with a diamine.

8. A curable resin according to claim 7 which is (a) and (a) is a cyanate ester in which each n in Formula I is zero.

9. A curable resin according to claim 7 which is a copolymer of (b) in which another component is (c) a maleimide or a prepolymer of a maleimide with a diamine.

10. A prepreg comprising the composition of claim 1.

11. A laminate comprising the cured or partially cured composition of claim 1.

12. A cured composition of claim 1 having a glass transition temperature of at least 150° C.

13. An article of manufacture prepared from a composition according to claim 1.

14. A shaped article comprising the cured or partially cured composition according to claim 1.

15. A reinforced composition comprising a cured or partially cured composition according to claim 1 and at least one reinforcing material.

* * * * *